United States Patent
Brown et al.

(10) Patent No.: US 6,639,079 B1
(45) Date of Patent: Oct. 28, 2003

(54) CHEMICAL PROCESS

(75) Inventors: Stephen Martin Brown, Huddersfield (GB); Martin Charles Bowden, Huddersfield (GB)

(73) Assignee: Syngenta Limited (GB)

( * ) Notice: Subject to any disclaimer, the term of this patent is extended or adjusted under 35 U.S.C. 154(b) by 0 days.

(21) Appl. No.: 10/031,626

(22) PCT Filed: Jul. 7, 2000

(86) PCT No.: PCT/GB00/02613

§ 371 (c)(1),
(2), (4) Date: May 28, 2002

(87) PCT Pub. No.: WO01/05766

PCT Pub. Date: Jan. 25, 2001

(30) Foreign Application Priority Data

Jul. 16, 1999 (GB) ............................................. 9916809

(51) Int. Cl.$^7$ ............................................. C07D 213/61
(52) U.S. Cl. ....................................................... 546/345
(58) Field of Search ......................................... 546/345

(56) References Cited

U.S. PATENT DOCUMENTS

| | | |
|---|---|---|
| 3,993,654 A | 11/1976 | Dean |
| 4,258,194 A | 3/1981 | Weis et al. |
| 4,804,764 A | 2/1989 | Murphy |
| 6,184,384 B1 * | 2/2001 | Lavin et al. ................. 546/345 |

OTHER PUBLICATIONS

Steiner et al, "A new Simple Synthesis, etc" Helvetica Chim. Acta, 65 (3), 1982, pp. 983–985.*
Martin et al, "Convenient Approaches to, etc" Tetrahedron, 41 (19), 1985, pp. 4057–4078.*
Eginhard Steiner et al.: "Eine neue, einfache synthese von 2,3,5–Trichloropyridin", Helvetica Chimica Acta, vol. 65, No. 3, 1982, pp. 983–985.
P. Sutter et al.: "The specificity of reductive dechlorination in the polychloropyridine series. Synthesis of 2,3, 5–Trichloro– and of 2,3,5,6–Tetrachloropyridine", Journal of Heterocyclic Chemistry, Heterocorporation, vol. 17, 1980, pp. 493–496.
Pierre Martin et al.: "Convenient Approaches to heterocycles via copper–catalysed additions of organic Polyhalides to activated olefins", Tetrahedron, vol. 41, No. 19, 1985, pp. 4057–4078.

* cited by examiner

Primary Examiner—Patricia L. Morris
(74) Attorney, Agent, or Firm—Thomas Hamilton

(57) ABSTRACT

A process for the preparation of 3,5-dichloropyridine comprising reacting a trichloropyridine, a tetrachloropyridine or pentachloropyridine with zinc metal, in the presence of an acidic compound and at a temperature in the range 50–120° C.

4 Claims, No Drawings

CHEMICAL PROCESS

This application is a 371 of PCT/GB00/02613, filed Jul. 7, 2000.

The present invention concerns a process for the preparation of 3,5-dichloropyridine. 3,5-Dichloropyridine is used as an intermediate in the chemical industry (especially in the agrochemical industry).

The present invention provides a process for the preparation of 3,5-dichloropyridine comprising reacting a trichloropyridine, a tetrachloropyridine or pentachloropyridine with zinc metal, in the presence of an acidic compound and at a temperature in the range 50–120° C.

Trichloropyridines include 2,3,5-trichloropyridine. Tetrachloropyridine is 2,3,4,5- or 2,3,5,6-tetrachloropyridine.

It is preferred that the process of the present invention is conducted in the presence of a protic solvent, such as water or an alcohol (for example sec-butanol). Also, the process of the present invention can be conducted in the presence of a mixture of solvents (such as a mixture of water and 1,4-dioxane).

Suitable acidic compounds include mineral acids (such as hydrochloric acid or sulphuric acid), organic acids (such as formic acid or acetic acid) or suitable ammonium salts (such as ammonium chloride).

In one aspect the present invention provides a process for preparing 3,5-dichloropyridine comprising reacting 2,3,5-trichloropyridine with zinc metal, in the presence of an acidic compound and at a temperature in the range 50–120° C.

In a further aspect the present invention provides a process for preparing 3,5-dichloropyridine comprising:

a) reacting acrylonitrile with anhydrous chloral in the presence of copper (I) chloride (and preferably in the presence of a suitable solvent (such as acetonitrile)) at a temperature in the range 100–200° C., to form 2,3,5-trichloropyridine; and, b) reacting the 2,3,5-trichloropyridine so formed with zinc metal, in the presence of an acidic compound and at a temperature in the range 50–120° C.

In a still further aspect steps (a) and (b) are conducted without purification of the intermediate 2,3,5-trichloropyridine.

In another aspect the present invention provides a process for the preparation of 3,5-dichloropyridine comprising reacting 2,3,4,5,6-pentachloropyridine with zinc metal, in the presence of an acidic compound and at a temperature in the range 80–120° C., wherein a quantity of 3,5-dichloropyridine (preferably sufficient so that, under the process conditions, the melting point of 2,3,4,5,6-pentachloropyridine is below 100° C. at the beginning of the process) is present at the beginning of the process.

The following Examples illustrate the invention.

EXAMPLE 1

This Example illustrates the preparation of 3,5-dichloropyridine from 2,3,4,5,6-pentachloropyridine

Procedure 1

Water (45 ml) was charged to a round bottomed flask fitted with temperature probe, a reflux condenser and an overhead stirrer (to provide good agitation during the course of the reaction). Agitation commenced and acetic acid (6 ml) was added followed by finely ground (mortar and pestle) 2,3,4,5,6-pentachloropyridine (10 g), then 3,5dichloropyridine (4.0 g) and finally zinc metal (20 g). The resulting mixture was heated to 81–82° C. for a total of 30 hours. (From time to time the cooler parts of the flask were gently warmed to melt small amounts of solid 3,5-dichloropyridine that had sublimed there.)

After 30 hours chromatography showed that all of the 2,3,4,5,6-pentachloropyridine had been consumed and only small amounts of tri- or tetra- chloropyridines remained.

Water (10 ml) was added to the reaction mixture followed by concentrated hydrochloric acid (10 ml). More water (20 ml) was then added.

The reactor was rigged for steam distillation and heated. Distillate was collected at a still head temperature of 98–100° C. Distillate was collected for a further 30 minutes and the distillate was a colourless oil plus water. (Further quantities of water were added during the steam distillation.) The oil crystallised on cooling.

The total distillate was extracted with dichloromethane (2×50 ml), the extracts were combined. dried over sodium sulphate and evaporated under reduced pressure to give 3,5-dichloropyridine as a white, low melting point solid (6.99 g, gas chromatography showed an 86.4 area % of 3,5-dichloropyridine equivalent to a yield of 44.6% based on the pentachloropyridine charged).

$^1$H NMR showed a 2 proton doublet at 8.48 ppm, and 1 proton triplet at 7.7 ppm.

Procedure 2

Water (45 ml) was charged to a round-bottomed flask fitted with temperature probe, an overhead stirrer to provide good agitation during the course of the reaction and a reflux condenser. Agitation commenced, acetic acid (6 ml) and 1,4-dioxane (8 ml) were added followed by finely ground (mortar and pestle) 2,3,4,5,6-pentachloropyridine (10 g) then 3,5-dichloropyridine (4.0 g) and finally zinc metal (20 g). The mixture was heated to 81–82° C. for a total of 29 hours. Chromatography confirmed that all of the pentahloropyridine had been consumed with small amounts of intermediate tri- and tetra- chloropyridines remaining.

Water (10 ml) was added followed by concentrated hydrochloric acid (10 ml) and prior to steam distillation a further quantity of water (20 ml) was added. The reactor was rigged for steam distillation and distillate was collected at a still head temperature of 98–100° C. Distilate was collected for a further 15 minutes to give a colourless oil plus water, the oil crystallising on cooling. (Further quantities of water were added during the steam distillation.)

The distillate was extracted with dichloromethane (2×50 ml), the extracts were combined, dried over sodium sulphate and evaporated under reduced pressure to give the title compound as a white low melting point solid (8.5 g, gas chromatography showed an 78 area% of 3,5-dichloropyridine equivalent to a yield of 60.8% based on the pentachloropyridine charged).

Procedure 3

2,3,4,5,6-Pentachloropyridine (5 g) was stirred together with glacial acetic acid (45 ml) and sodium acetate (5.4 g), zinc metal dust (4.33 g) and the mixture the heated to 100° C. over 30 minutes. After 4 hours a white precipitate had formed and analysis showed that 50% conversion had occurred. Further zinc dust (4.33 g) was added and stirring and heating were continued for a further hour after which time analysis showed the reaction to be complete.

Water (75 ml) was added and the reactor set for steam distilation. Distillate was collected at a head temp up to 101°

C. and continued until the head temperature began to rise. The condenser was washed through with dichloromethane (25 ml) to dissolve the solid product that had collected therein. The organic phase was then separated from the aqueous phase. The aqueous phase extracted twice with dichloromethane. The organic extracts were combined, dried over magnesium sulphate and evaporated under reduced pressure to give the title compound as a white solid (1.9 g, yield 65% on pentachloropyridine charged).

EXAMPLE 2

This Example illustrates the preparation of 3,5-dichloropyridine from 2,3,5-trichloropyridine.

2,3,5-Trichloropyridine (3.6 g) was charged to a round bottomed flask containing water (9.0 ml) and acetic acid (2.0 ml). The mixture was agitated with a magnetic follower, zinc metal powder (2.5 g) added and the mixture was heated to 95° C. The reaction was monitored by chromatography and after 1 hour all of the 2,3,5-trichloropyridine had been consumed. The mixture was steam distilled to give water plus an oil that solidified on cooling. The solid was dissolved in dichloromethane (20 ml), the organic phase was separated, dried by passage under gravity through a filter paper and evaporated under reduced pressure to give the title compound as a low melting point solid (2.51 g, yield of 87.3%). Material confirmed as 3,5-dichloropyridine by comparative chromatography and $^1$H NMR.

EXAMPLE 3

This Example illustrates the preparation of 3,5-dichloropyridine from 2,3,5-trichloropyridine.
Step 1

Copper (I) chloride (100 mg) was charged to a glass Carrius™ tube together with acetonitrile (7.5 ml) and acrylonitrile (1 g) and anhydrous chloral (3.3 g). The mixture was heated to 120° C. for 16 hours and allowed to cool to room temp whilst a small sample was withdrawn for analysis. The reaction mixture was reheated for 3 hours at 175° C. and then allowed to cool again. Chromatography confirmed the presence of 2,3,5-trichloropyridine in the reaction mass.
Step 2

To approximately half the crude reaction mass from Step 1 was added water (15 ml), zinc metal powder (2.0 g) and acetic acid. The mixture was heated to 65° C. After 2 hours 25 minutes a further quantity of zinc metal (0.5 g) was added and heating was continued for a further 2 hours 50 minutes. The resulting mixture was steam distilled until approximately 8 mls of distillate had been collected. The addition of water (10 ml) to the distillate caused a white solid to precipitate. The resulting distillate mixture was extracted with dichloromethane (20 ml) and the organic and inorganic phases were added to water (50 ml). The organic phase was separated and the aqueous phase re-extracted with a further quantity of dichloromethane (20 ml). The organic extracts were combined, washed with water (50 ml), dried over magnesium sulphate, the drying agent was filtered off and washed with dichloromethane. The filtrate was evaporated under reduced pressure to give the title compound as a white solid (0.531 g, approximate yield of 42% based on acrylonitrile charged).

EXAMPLE 4

This Example illustrates the preparation of 3,5-dichloropyridine from 2,3,4,5-tetrachloropyridine.

2,3,4,5-Tetrachloropyridine (1 g) was charged to a reaction tube containing water (2 ml), 1,4-dioxane (6 ml), ammonium chloride (0.8 g) and zinc powder (1.5 g). Agitation was commenced (magnetic follower) and the reaction tube heated to 90–92° C. for 8 hours. Gas chromatography of the reaction mixture showed that it comprised a monochloropyridine 1.8% and 3,5-dichloropyridine 98%.

EXAMPLE 5

This Example illustrates the preparation of 3,5-dichloropyridine from 2,3,5,6-tetrachloropyridine.

2,3,5,6-Tetrachloropyridine (1 g) was charged to a reaction tube containing water (2 ml), 1,4-dioxane (6 ml), ammonium chloride (0.8 g) and zinc powder (1.5 g). Agitation was commenced (magnetic follower) and the reaction tube heated to 90–92° C. for 12 hours. Gas chromatography of the reaction mixture showed that it comprised: 3,5-dichloropyridine 77.8%, 2,3,5-trichloropyridine 7.7% and 2,3,5,6-terachloropyridine 14.5%.

What is claimed is:

1. A process for preparing 3,5-dichloropyridine comprising:
    a) reacting acrylonitrile with anhydrous chloral in the presence of copper (I) chloride at a temperature in the range 100–200° C., to form 2,3,5-trichloropyridine; and,
    b) reacting the 2,3,5-trichloropyridine so formed with zinc metal, in the presence of an acidic compound and at a temperature in the range 50–120° C.

2. A process according to claim 1 in which steps (a) and (b) are conducted without purification of the intermediate 2,3,5-trichloropyridine.

3. A process according to claim 1 in which the reaction of step (a) is conducted in the presence of a suitable solvent.

4. A process according to claim 3 in which the solvent is acetonitrile.

* * * * *